(12) United States Patent
Hubbell et al.

(10) Patent No.: US 6,986,281 B1
(45) Date of Patent: Jan. 17, 2006

(54) EXFILTROMETER APPARATUS AND METHOD FOR MEASURING UNSATURATED HYDROLOGIC PROPERTIES IN SOIL

(75) Inventors: Joel M. Hubbell, Idaho Falls, ID (US); James B. Sisson, Idaho Falls, ID (US); Annette L. Schafer, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 0 days.

(21) Appl. No.: 10/883,254

(22) Filed: Jun. 30, 2004

(51) Int. Cl.
*E21B 47/00* (2006.01)
(52) U.S. Cl. .................. 73/152.01; 73/152.09; 73/152.11; 73/73; 73/170.32
(58) Field of Classification Search ............ 73/73, 73/152.01, 152.09, 152.11, 170.32
See application file for complete search history.

(56) References Cited

U.S. PATENT DOCUMENTS

| | | | |
|---|---|---|---|
| 3,690,166 A * | 9/1972 | Grice et al. ............ 73/84 |
| 4,137,931 A | 2/1979 | Hasenbeck |
| 4,540,936 A | 9/1985 | Walsh |
| 4,657,039 A | 4/1987 | Bireley et al. |
| 5,022,262 A * | 6/1991 | Hulsbergen et al. ..... 73/170.32 |
| 5,445,178 A | 8/1995 | Feuer |
| 5,644,947 A | 7/1997 | Hubbell et al. |
| 5,758,538 A | 6/1998 | Hubbell et al. |
| 5,915,476 A | 6/1999 | Hubbell et al. |
| 6,263,726 B1 | 7/2001 | Hubbell et al. |
| 6,289,725 B1 | 9/2001 | Hubbell et al. |
| 2003/0140690 A1 * | 7/2003 | Faybishenko ............ 73/152.18 |

OTHER PUBLICATIONS

"Methods of Soil Analysis, Part 4 Physical Methods" Dane and Topp, 2002.

* cited by examiner

*Primary Examiner*—John E. Chapman
*Assistant Examiner*—Katina Wilson
(74) *Attorney, Agent, or Firm*—Dahl Osterloth, LLP

(57) ABSTRACT

Exfiltrometer apparatus includes a container for holding soil. A sample container for holding sample soil is positionable with respect to the container so that the sample soil contained in the sample container is in communication with soil contained in the container. A first tensiometer operatively associated with the sample container senses a surface water potential at about a surface of the sample soil contained in the sample container. A second tensiometer operatively associated with the sample container senses a first subsurface water potential below the surface of the sample soil. A water content sensor operatively associated with the sample container senses a water content in the sample soil. A water supply supplies water to the sample soil. A data logger operatively connected to the first and second tensiometers, and to the water content sensor receives and processes data provided by the first and second tensiometers and by the water content sensor.

21 Claims, 7 Drawing Sheets

EXFILTROMETER APPARATUS AND METHOD FOR MEASURING UNSATURATED HYDROLOGIC PROPERTIES IN SOIL

GOVERNMENT RIGHTS

The United States Government has certain rights in this invention pursuant to Contract No. Contract No. DE-AC07-99ID13727, and Contract No. DE-AC07-05ID14517 between the U.S. Department of Energy and Battelle Energy Alliance, LLC.

FIELD OF THE INVENTION

This invention relates to apparatus and methods for measuring unsaturated hydrologic properties in porous media.

BACKGROUND

Hydrologic properties may be estimated in the laboratory on field cores or from special tests conducted in the field. By determining soil water content ($\theta$) and water potential ($\Psi m$), various properties of a sample including soil water flux (q), hydraulic gradient (I), hydraulic conductivity (K) and the soil water retention curve [soil water potential ($\Psi m$) versus water content ($\theta$)] may be estimated. This data is necessary for site characterization, including determination of recharge at waste disposal, agricultural and other sites, as well as for ground water protection and conservation.

Laboratory testing requires removal of a sample from its native environment, causing disturbance to the sampling location. The sample must be transported to the laboratory for testing by a skilled technician. Labor and expense is involved with securing an undisturbed transport of the sample. The laboratory tests normally require several weeks to perform. The data obtained may be incomplete, particularly in the wet range, as the pristine condition of the sample is compromised. Thus, laboratory testing is not optimum as it is time consuming, expensive, and incomplete results may be obtained.

Field testing also requires several weeks to months to perform. While the sample may be analyzed in its native environment, other factors, including weather, temperature and wildlife may affect the testing. Similar to laboratory testing, field testing is also expensive in time, money and human resources to perform.

Estimation of unsaturated hydraulic properties under field conditions is frequently accomplished using the instantaneous profile method (IPM) (Davidson, et al., 1969). According to the IPM, when water movement takes place in a one-dimensional system, the soil moisture equation can be written as (Davidson, et al., 1969):

$$\frac{dW(z,t)}{dt} = q(0,t) - q(z,t) \quad [1]$$

Where q(z,t) is the Darcian flux ($LT^{-1}$) at depth z and time t, W is total water stored above z or $$W(z,t) = \int_0^z \theta(z,t)^{dt} \quad [2]$$

When the soil column is undergoing drainage only q(0,t)=0, Equation [1] becomes:

$$\frac{dW(z,t)}{dt} = -q(z,t) \quad [3]$$

Darcian flux is given by:

$$q(z,t) = -K\frac{\partial H}{\partial Z} \quad [4]$$

Where K is hydraulic conductivity ($LT^{-1}$), H is total water potential (L) and q is approximated as:

$$q(z,t) \cdot - \frac{dW(z,t) - W(z, t-\Delta t)}{\Delta t} \quad [5]$$

When the gradient term is approximated as a difference equation, it results in the IPM for obtaining hydraulic conductivity as a function of either water content or water potential:

$$K \cdot q(z,t)\frac{\Delta_z}{\Delta H} \quad [6]$$

Implementing the IPM in the field requires wetting the soil to field saturation, covering the experiment to prevent evaporation (i.e., set q(0,t)=0) and allowing the soil to drain freely. Since the IPM requires infiltration of 1 to 10 m³ of water, as well as instrument installations at multiple depths, the method is not being used at many hazardous waste sites. The entire IPM can take several weeks in the field (Davidson, et al., 1969; Sisson, et al., 1980). The apparatus and methods disclosed herein allow rapid determination of the soil hydraulic properties while using the IPM model.

SUMMARY

Exfiltrometer apparatus for estimating at least one unsaturated hydrologic property of a soil sample may comprise a container for holding soil. A sample container for holding the sample soil is positionable with respect to the container so that the sample soil contained in the sample container is in communication with soil contained in the container. A first tensiometer operatively associated with the sample container senses a surface water potential at about a surface of the sample soil contained in the sample container. A second tensiometer operatively associated with the sample container senses a first subsurface water potential below the surface of the sample soil. A water content sensor operatively associated with the sample container senses a water content in the sample soil. A water supply supplies water to the sample soil. A data logger operatively connected to the first and second tensiometers, and to the water content sensor receives and processes data provided by the first and second tensiometers and by the water content sensor.

Exfiltrometer apparatus for estimating at least one unsaturated hydrologic property of in-situ soil in a soil environment comprises a sample container that is positionable within the soil environment so that a distal end of the sample container penetrates in-situ soil in the soil environment. A water supply operatively associated with the sample container introduces water to an in-situ soil sample isolated by the sample container. A first tensiometer operatively associated with the sample container senses a surface water potential at about a surface of the in-situ soil sample isolated by the sample container. A second tensiometer operatively associated with the sample container senses a first subsurface water potential below the surface of the isolated in-situ soil sample. A water content sensor operatively associated with the sample container senses a water content in the isolated in-situ soil sample. A data logger operatively connected to the first and second tensiometers and to the water content sensor receives and processes data provided by the first and second tensiometers and by the water content sensor.

A method of estimating at least one unsaturated hydrologic property of sample soil comprises providing an amount of soil; positioning a sample container on the soil; filling the sample container with sample soil so that sample soil within the sample container communicates with the soil; adding water to the sample soil until the sample soil is substantially saturated; allowing the sample soil to dry by allowing the soil to absorb water from the sample soil contained in the sample container; and sensing at least a surface water potential, a subsurface water potential, and a water content of the sample soil as the sample soil dries.

A method of estimating at least one unsaturated hydrologic property of in-situ soil in a soil environment: Positioning a sample container within the soil environment so that a substantially open distal end of the sample container penetrates in-situ soil in the soil environment, the sample container isolating an in-situ soil sample within an interior region defined by the sample container; adding water to the sample container until the in-situ soil sample isolated therein is substantially saturated; allowing the isolated in-situ soil sample to dry using in-soil within the soil environment and not isolated by the sample container to pull water from the isolated in-situ soil sample; and sensing at least a surface water potential, a subsurface water potential, and a water content of the isolated in-situ soil sample as the isolated in-situ soil sample dries.

BRIEF DESCRIPTION OF THE DRAWING

Illustrative and presently preferred embodiments of the invention are shown in the accompanying drawing in which.

DETAILED DESCRIPTION

Figure 1:
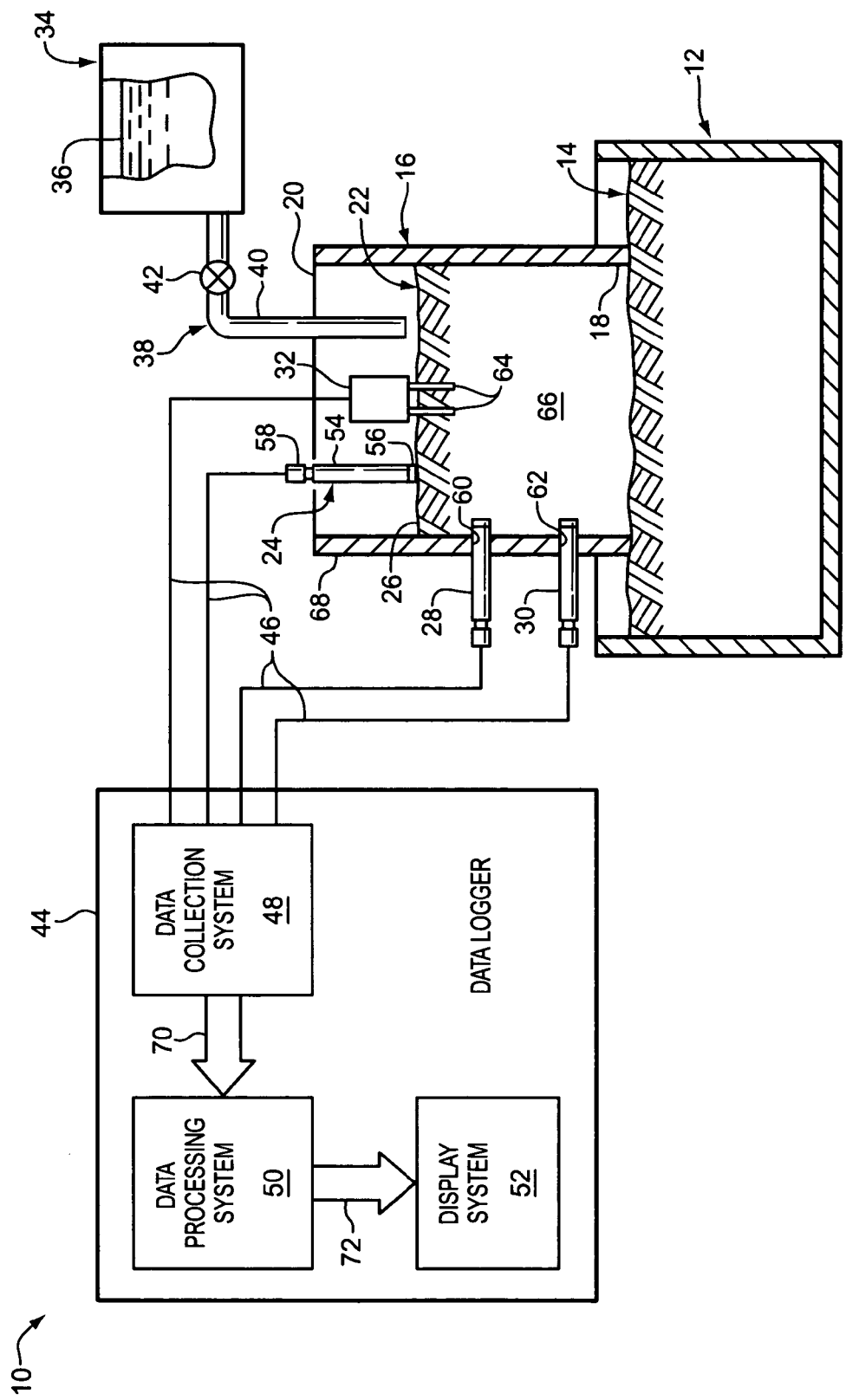
FIG. 1 is a side view schematic representation of one embodiment of an exfiltrometer apparatus for determining unsaturated hydrologic properties of sample soil.

Exfiltrometer apparatus 10 according to one embodiment of the present invention is illustrated in FIG. 1 and may used to estimate at least one unsaturated hydrologic property of soil. As will be described in greater detail below, at least one unsaturated hydrologic property that may be estimated using the methods and apparatus of the present invention includes, but is not limited to, soil water flux, hydraulic gradient, hydraulic conductivity, soil water potential, and water content. The soil water retention curve, i.e., soil water potential versus water content can also be determined.

Referring now primarily to FIG. 1, one embodiment of exfiltrometer apparatus 10 according to the present invention may comprise a container 12 for holding an amount of soil 14. A sample container 16 having substantially open ends 18, 20 is positionable with respect to the container 12 when the container 12 contains soil 14 so that sample soil 22 contained in the sample container 16 is in communication with (e.g., contacts) soil 14 contained in the container 12. This is the arrangement illustrated in FIG. 1.

A first tensiometer 24 is operatively associated with the sample container 16 so that the first tensiometer 24 senses a surface water potential at about a surface 26 of the sample soil 22 contained in the sample container 16. A second tensiometer 28 is operatively associated with the sample container 16 so that the second tensiometer 28 senses a first subsurface water potential below the surface 26 of sample soil 22 contained in the sample container 16. As will be described in greater detail below, the exfiltrometer apparatus 10 may optionally comprise additional tensiometers, such as an optional third tensiometer 30, for sensing water potential at other subsurface locations. For example, the optional third tensiometer 30 illustrated in FIG. 1 is operatively associated with the sample container 16 so that the third tensiometer 30 senses a second subsurface water potential below the surface 26 of sample soil 22 contained within sample container 16. In the embodiment illustrated in FIG. 1, the second subsurface water potential corresponds to a subsurface position below the subsurface position at which the first subsurface water potential is sensed by the second tensiometer 28. The exfiltrometer apparatus 10 may also be provided with a water content sensor 32 that is operatively associated with the sample container 16 so that the water content sensor 32 senses a water content in the sample soil 22 contained in the sample container 16.

The exfiltrometer apparatus 10 also comprises a water supply or reservoir 34 that is operatively associated with the sample container 16. The water supply or reservoir 34 contains a supply of water 36 which may be delivered to sample soil 22 contained in sample container 16 via a suitable water conduit system 38, such as pipe 40. The pipe 40 may be provided with a valve 42 to allow the water 36 to be delivered to the sample soil 22 according to the appropriate schedule (e.g., times and rates), as will be described in greater detail below.

The exfiltrometer apparatus 10 also comprises a data logger system 44. The data logger system 44 is operatively connected to the tensiometers 24, 28, (and, optionally third tensiometer 30), as well as to the water content sensor 32 by any convenient means, such as, for example, via wire leads 46. As will be described in greater detail below, the data logger system 44 may comprise various subsystems, such as data collection system 48, data processing system 50, and display system 52 to allow the data logger system 44 to receive and process data provided by the various tensiometers 24, 28 (and, optionally third tensiometer 30), as well as by the water content sensor 32. Thereafter, data indicative of at least one unsaturated hydrologic property of the sample soil 22 may be presented on the display system 52. Alternatively, data indicative of the at least one unsaturated hydrologic property of the sample soil 22 may remain in electronic form so that it may be transferred from the data logger system 44 to an external system (not shown), such as a personal computer system for further processing/manipulation and/or display.

The exfiltrometer apparatus 10 may be operated as follows to estimate at least one unsaturated hydrologic property of sample soil 22. As a first step, an amount of soil 14 may be provided to container 12. The soil 14 acts as a sink for water contained in the sample soil 22. The sample container 16 is then positioned on the soil 14 in container 12 so that open end 18 of sample container 16 is resting on the soil 14. The soil 22 in the sample container 16 can be an undisturbed or recompacted sample, dependant on the test requirements. The sample soil 22 (e.g. soil to be sampled) within sample container 16 then communicates with soil 14 in the container 12. Water 36 from water supply or reservoir 34 is then added to the sample soil 22 until the sample soil 22 is substantially saturated. For example, sample soil 22 is substantially saturated when tensiometers 28 and 30 indicate saturated readings. Thereafter, the sample soil 22 is allowed to dry by allowing the soil 14 in container 12 to act as a sink to absorb water 36 from the sample soil 22 contained in the sample container 16. The next step comprises sensing at least a surface water potential, a subsurface water potential, and a water content of the sample soil 22 as the sample soil 22 dries over time. Thereafter, the water potential and water content data values are sent to the data logger system 44 which estimates at least one unsaturated hydrologic property of the sample soil 22. Other techniques to apply a tension to soil 22 may be substituted for this configuration such as a hanging water column or tension plate apparatus.

The exfiltrometer apparatus according to the present invention collects or acquires at least the in-situ water pressure potential (e.g., from the tensiometers 24, 28, and, optional tensiometer 30) and the volumetric water content (e.g., from the water content sensor 32) of the soil 22. From these measurements, at least one unsaturated hydrologic property of the soil may be estimated. As mentioned above, unsaturated hydrologic properties include, but are not limited to, soil water flux, hydraulic gradient, hydraulic conductivity, soil water potential, and water content. A soil water retention curve (i.e., soil water potential versus water content) may also be estimated. The unsaturated hydrologic properties may be estimated from the data obtained by the exfiltrometer 10 using the instantaneous profile method (IPM), although other methods may also be used. The instantaneous profile method (IPM), also referred to as the internal drainage method, is based on the analysis of changes in volumetric water content and of soil water pressure head within the soil profile during redistribution following infiltration. Two assumptions are made: (i) there is no evaporation through the soil surface, and (ii) there is one-dimensional, vertical flow downward only. The IPM method requires the simultaneous measurements of water content and soil water pressure head at different soil depths as time progresses during drainage following infiltration. *Methods of Soil Analysis, Part 4 Physical Methods*, Dane, Jacob H., Topp, G. Clarke.

One advantage of the exfiltrometer apparatus according to the present invention is that it may be used in the laboratory or at land-surface in order to determine at least one unsaturated hydrologic property of sample soil. By land-surface, it is meant that the exfiltrometer may be placed into the soil-surface to measure unsaturated hydrologic properties of the surface soil within container 16, using the soil immediately below to act as the soil 14 within container 12. The exfiltrometer apparatus comprises relatively simple components and is readily mobile and easy to set-up at any of a wide variety of locations. The apparatus may be run rapidly and without operator assistance following the initial set-up. A test run may be performed within twenty-four (24) hours over a wider range of values compared with much longer test runs that could be performed in the field or laboratory. The test runs may be performed with minimal disturbance of the sampling location thereby providing more representative results. Overall, exfiltrometer apparatus according to the present invention provides an improved, faster, and less expensive estimation of unsaturated hydrologic properties.

Having briefly described one embodiment 10 of exfiltrometer apparatus according to the present invention, as well as a method for estimating at least one unsaturated hydrologic property of sample soil, the various example embodiments and methods of the present invention will now be described in detail. However, before proceeding with the detailed description, it should be noted that while the various example embodiments of exfiltrometer apparatus are shown and described herein as they could be used to measure water potential and water content from which at least one unsaturated hydrologic property may be estimated, the various embodiments also could be used in any of a wide range of other applications wherein it is required to measure capillary-water content relationship. Consequently, the present invention should not be regarded as limited to the particular applications shown and described herein.

With the foregoing considerations in mind, one embodiment of exfiltrometer apparatus 10 according to the present invention is illustrated in FIG. 1 and may comprise a container 12 for holding soil 14. The container 12 may comprise any of a wide range of containers suitable for holding an amount of soil 14, as would be obvious to persons having ordinary skill in the art after having become familiar with the teachings provided herein. Accordingly, the present invention should not be regarded as limited to a container 12 comprising any particular configuration or having any particular capacity. The container 12 may be constructed from any of a wide range of materials (e.g., steel, plastic, wood, etc) suitable for holding the soil 14 that would be suitable for the intended application. Therefore, the present invention should not be regarded as limited to a container 12 comprising any particular material. However, by way of example, in one preferred embodiment, the container 12 comprises a container having a generally rectangular configuration and fabricated from metal. The container 12 in one embodiment has an internal volume or capacity of about 0.3 cubic meters ($m^3$), thus is capable of holding a like amount of soil 14. However, because the specifics of container 12 could be easily arrived-at by persons having ordinary skill in the art after having become familiar with the teachings of the present invention and after considering the particular application, the particular container 12 that may be utilized in one preferred embodiment of the present invention will not be described in further detail herein.

The soil 14 provided in the container 12 may comprise any of a wide range of soils, as would be obvious to persons having ordinary skill in the art after having become familiar with the teachings of the present invention. It is generally preferred, but not required, that the soil 14 comprise a soil having a tension of about 300 cm.

The sample container 16 may comprise a structure suitable for holding sample soil 22 having open ends 18 and 20. The arrangement is such that the sample container 16 defines an interior region 66 generally between the open ends 18 and 20, as best seen in FIG. 1. The sample container 16 is sized so that the open end 18 thereof may be received by the soil 14 in container 12 so that sample soil 22 contained in sample container 16 is in communication with the soil 14 in container 12 via open end 18 of sample container 16. As was the case for the container 12, the sample container 16 may comprise any of a wide range of configurations and may be fabricated from any of a wide range of materials suitable for the intended application. Consequently, the sample container 16 should not be regarded as limited to any particular configuration or material. However, by way of example, in one preferred embodiment, the sample container 16 comprises a generally cylindrically shaped tube or pipe-like member having an internal diameter of about 20 cm and a length (i.e., height) of about 30 cm.

The sample container 16 may be made from any of a wide range of materials, such as steel, plastic, or wood, suitable for the intended application. Consequently the present invention should not be regarded as limited to any particular material. However, by way of example, in one embodiment, the sample container 16 is fabricated from metal.

The first tensiometer 24 is operatively associated with the sample container 16 so that the first tensiometer 24 senses a surface water potential, i.e., a water potential at about the surface 26 of the sample soil 22. The first tensiometer 24 may be used to record the rate of pressure change, which may then be used to estimate the "rate of fall" of the ponded water on the surface 26 of sample soil 22 after infiltration, i.e., after water 36 is introduced to the sample soil 22 to substantially saturate the sample soil 22. The "rate of fall" provides the volume of water moving into the sample soil 22 and is used to estimate the soil water flux into the sample soil 22. This data may be used to estimate the hydraulic conductivity. First tensiometer 24 indicates when the ponded water is imbibed into the sample soil 22, i.e. when the sample soil 22 transitions from substantially saturated to unsaturated and then obtains initial tensiometric data for drainage near the point of saturation. Generally, then, first tensiometer 24 measures how tightly water is held by the soil in which it is contained. That is, tensiometer 24 is used to measure soil water potential at the surface 26 of the sample soil 22.

Tensiometer 24 may comprise any of a wide range of tensiometers that are known in the art and described in the patent literature. For example, tensiometer 24 may comprise a tensiometer of the types disclosed in U.S. Pat. No. 5,644,947 to Hubbell et al., and U.S. Pat. No. 6,289,725 to Hubbell et al., (both of which are incorporated herein by reference for all that they disclose), thus will not be described in great detail herein. However, in order to provide a background for better understanding the present invention, one embodiment of a tensiometer, such as tensiometer 24, that may be utilized in the present invention will be briefly described herein.

Generally speaking, tensiometer 24 comprises a sealed chamber 54 that is filled with water (not shown). The tensiometer 24 is provided with a semi-permeable membrane 56 that allows water to pass through while restricting air movement. Semi-permeable membrane 56 may be comprised of porous stainless steel or any other suitable material such as porous ceramic, plastic or glass. The nominal pore size of the semi-permeable membrane 56 is approximately about 0.2 microns to about 1.0 microns in width. The semi-permeable membrane 56 of the tensiometer 24 is placed in contact with material, generally, soil, (e.g., sample soil 22) to be measured. Water (not shown) inside the chamber 54 moves through the semi-permeable membrane 56 until the pressure inside the chamber 54 is equivalent to the pressure in the soil being measured. A pressure transducer 58 senses the water pressure within the chamber 54 of tensiometer 24 and produces output data that are related to the pressure of the water within the chamber 54.

In the embodiment illustrated in FIG. 1, the first tensiometer 24 is mounted within the sample container 16 so that the semi-permeable membrane 56 is in contact with the surface 26 of sample soil 22. Any of a wide variety of mounting systems may be used to mount the first tensiometer 24 within the sample container 16, as would be obvious to persons having ordinary skill in the art after having become familiar with the teachings of the present invention. Consequently, the particular mounting system that may be used to mount the first tensiometer 24 within the sample container 16 will not be described in further detail herein.

In another embodiment, the first tensiometer 24 may be mounted so that it extends through an opening (not shown) provided in a side wall 68 sample container 16 so that the semi-permeable membrane (e.g., 56) of the first tensiometer 24 is positioned at about the surface 26 of the sample soil 22 contained in the sample container 16. The arrangement would be similar to that used to mount the second tensiometer 28, described below and illustrated in FIG. 1.

The second tensiometer 28 is operatively associated with the sample container 16 so that the second tensiometer 28 senses a first subsurface water potential below the surface 26 of sample soil 22 contained in the sample container 16. In the embodiment illustrated in FIG. 1, the side wall 68 of sample container 16 is provided with a generally transversely-oriented bore or opening 60 therein sized to receive the second tensiometer 26. While the opening 60 may be located so as to position the second tensiometer 28 at any of a wide range of subsurface locations, the opening 60 in one preferred embodiment is located so that the second tensiometer 28 is located about 5 cm below the surface 26 of sample soil 22.

Figure 2:
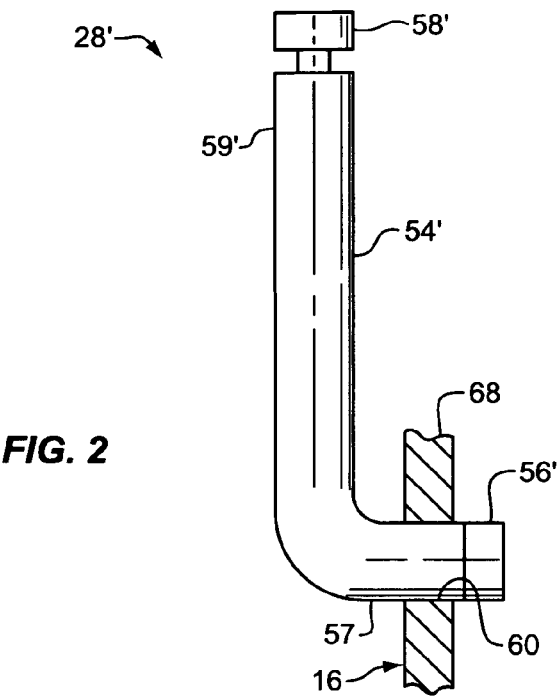
FIG. 2 is a side view in elevation of a second tensiometer configuration that may be utilized in the exfiltrometer apparatus.

The second tensiometer 28 may be identical to the first tensiometer 24 already described. Alternatively, the second tensiometer 28 may comprise another embodiment 28' illustrated in FIG. 2. The alternate embodiment tensiometer 28' illustrated in FIG. 2 may comprise an L-shaped chamber 54' having a semi-permeable membrane 56' positioned on the base or horizontal end 57'. A pressure transducer 58' operatively associated of L-shaped chamber 54' senses the pressure of water (not shown) contained within the L-shaped chamber 54'. The alternative embodiment 28' may be substituted for the tensiometer 28 illustrated in FIG. 1. The base or horizontal end 57' of the L-shaped chamber 54' having the semi-permeable membrane 56' extends through through the subsurface opening 60 provided in the side wall 68 of sample container 16. The long or vertical end 59' of the L-shaped chamber 54' may then be made to extend generally upwardly along the side of the sample container 16, although this is not required. The particular orientation afforded by the alternative embodiment of second tensiometer 28' may be advantageous in circumstances wherein space is limited around the exfiltrometer apparatus 10.

As mentioned above, the exfiltrometer apparatus 10 may be provided with additional tensiometers, such as third tensiometer 30, for sensing water potential at additional subsurface locations. Such additional tensiometers, such as third tensiometer 30, may be used if the hydraulic gradient in the sample soil 22 is not assumed to be fixed. Alternatively, if the hydraulic gradient in the sample soil 22 is assumed to be fixed, or if it is not desired to provide additional data regarding the subsurface water potential, then such additional tensiometers, such as third tensiometer 30, may be omitted. However, if the additional data provided by a third tensiometer is desired, then the third tensiometer 30 may be operatively associated with the sample container 16 so that the third tensiometer 30 senses a second subsurface water potential below the surface 26 of sample soil 22 contained in the sample container 16. In the embodiment illustrated in FIG. 1, the second subsurface water potential is sensed at a location that is below the location at which the first subsurface water potential is sensed by tensiometer 28. The third tensiometer 30 may be mounted in a manner similar to that used for the second tensiometer 28. For example, the third tensiometer 30 may be mounted to the sample container 16 so that the third tensiometer 30 extends through a generally transversely-oriented bore or opening 62 provided in the side wall 68 of sample container 16. As mentioned, the opening 62 may be located to position the third tensiometer 30 at a location below the location of the second tensiometer 28, as is best seen in FIG. 1. By way of example, in one preferred embodiment, the second opening 62 is located so that the third tensiometer 30 is located about 10 cm below the surface 26 of sample soil 22, although other locations may be used.

The third tensiometer 30 may be identical to the first tensiometer 24 and the second tensiometer 28. Alternatively, the third tensiometer 30 could comprise a generally L-shaped tensiometer embodiment, similar to the L-shaped tensiometer embodiment 28' already described and illustrated in FIG. 2.

The exfiltrometer apparatus 10 may also be provided with a water content sensor 32, as best seen in FIG. 1. In the embodiment illustrated in FIG. 1, water content sensor 32 comprises a pair of probes 64 that extend into the sample soil 22 so that the probes 64 are generally perpendicularly-oriented with respect to the second and third tensiometers 28 and 30. Water content sensor 32 measures the water content for the chosen region or stratigraphic interval of the sample soil 22. As will be described in further detail below, soil water flux may be estimated from the rate of change in water content divided by the volume of water content sensed by the water content sensor 32.

Water content sensor 32 may comprise any of a wide range of water content sensors well-known in the art and that are readily commercially available. Consequently, the present invention should not be regarded as limited to any particular type of water content sensor. However, by way of example, in one preferred embodiment, water content sensor 32 may comprise a time domain reflectometer type of sensor, such as model CS 615, available from Campbell Scientific, Inc., of Logan, Utah. Alternatively, the water content sensor 32 may comprise a capacitance type of sensor, such as the "ECH$_2$O" type of water moisture probe available from Decagon Devices, Inc., of Pullman, Wash.

Figure 3:
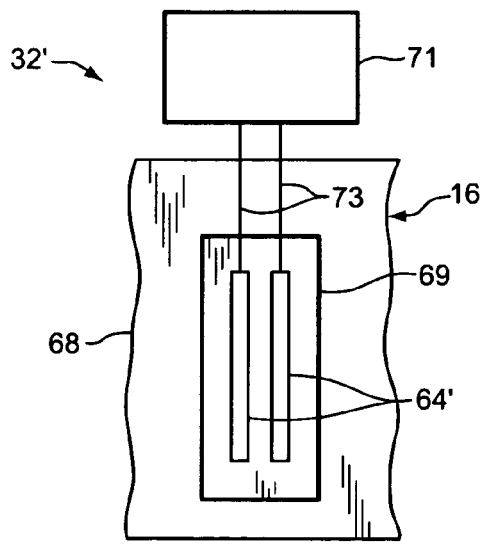
FIG. 3 is a partial side view in elevation of a second water content sensor configuration that may be utilized in the exfiltrometer apparatus.

Other arrangements are possible for the water content sensor 32. For example, and with reference now to FIG. 3, a second embodiment of a water content sensor 32' may be attached to the inner portion of side wall 68 of sample container 16. If the sample container 16 is fabricated from an electrically conductive material (e.g., steel), an insulating or dielectric backing material 69 may be placed between probes 64' of water content sensor 32'. The dielectric backing material 69 may comprise paint, plastic with adhesive or any other type of non-conductive backing. The probes 64' may comprise metal strips having a width of about 6.4 mm and a thickness of about 0.75 mm, although other configurations are possible. The probes 64' may be positioned on the dielectric backing material 69 and may be applied as a decal with adhesive, by lithography or other method. The electronic circuitry 71 comprising the water content sensor 32' are operatively attached to the probes 64' via wires 73. The electronic circuitry 71 may be mounted to the sample container 16 or located elsewhere, if desired.

Figure 4:
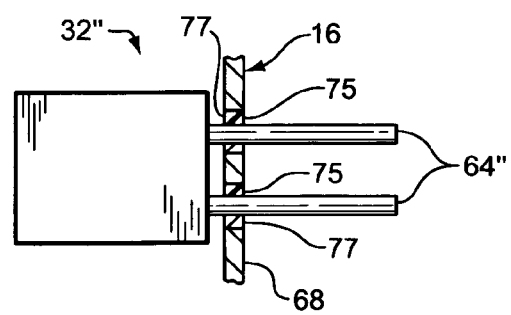
FIG. 4 is a partial side view in elevation of a third water content sensor configuration that may be utilized in the exfiltrometer apparatus.

In yet another embodiment, illustrated in FIG. 4, a water content sensor 32" may be mounted so that the probes 64" extend through the side wall 68 of the sample container 16 and into the sample soil 22 (FIG. 1) contained therein. In this arrangement, the side wall 68 of sample container 16 is provided with at least one opening, such as a pair of openings 75, sized to pass the probes 64" of water content sensor 32". A suitable potting or sealing material 7 may be used to seal the annulus defined between the openings 75 and the probes 64".

Referring back now to FIG. 1, the exfiltrometer apparatus 10 also comprises a water reservoir or supply system 34 that is operatively positioned with respect to the sample container 16. The water supply system 34 contains a supply of water 36 which may be delivered to the sample soil 22 contained in the sample container 16. In the embodiment shown and described herein, the water 36 from water supply 34 is delivered to the sample soil 22 via a water conduit system 38 comprising a pipe 40 and a valve 42. The valve 42 may be manually or automatically operated so as to control the flow of water 36 to allow the same to be delivered to the sample soil 22 according to the appropriate schedule (e.g., times and rates). However, because the various devices comprising water supply system 34 are well-known in the art and could be easily provided by persons having ordinary skill in the art after having become familiar with the teachings of the present invention, the particular components of the water supply system 34 and water conduit system 38 will not be described in further detail herein.

The exfiltrometer apparatus 10 is also provided with a data logger system 44. Data logger system 44 is operatively connected to the tensiometers 24, 28, (and, optionally, tensiometer 30) as well as to the water content sensor 32 by any convenient means, such as by wire leads 46. The data logger system 44 comprises a data collection system 48 which collects data from the various sensors (e.g., 24, 28, 30, and 32), and processes the data as necessary to produce conditioned data 70 suitable for further processing by the data processing system 50. The data processing system 50 is operatively associated with the data collection system 48 and receives conditioned data 70 therefrom. The data processing system 50 may be provided with suitable software routines to process the conditioned data 70 from the data collection system 48 to produce output data 72 containing at least one unsaturated hydrologic property of the sample soil 22. For example, the software routines executed by the data processing system 50 may process the conditioned data 70 in accordance with one or more of the equations identified herein to produce the desired at least one unsaturated hydrologic property of the sample soil 22. However, because such software routines are within the level of a person having ordinary skill in the art and could be easily developed after becoming familiar with the teachings provided herein, the particular software routines that may be utilized to produce the at least one unsaturated hydrologic property of the sample soil 22 will not be described in further detail herein. The data logger system 44 may also be provided with a display system 52, such as a LCD flat-panel display (not shown) suitable for displaying the output data 72 from the data processing system 50. Alternatively, other types of display systems that are now known in the art or that may be developed in the future may also be used. The data logger system 44 may also provide data in electronic form to an external device (not shown), such as a personal computer, for additional processing/manipulation and display.

The data logger system 44 may comprise any of a wide range of data logger systems that are well-known in the art and that are readily commercially available. Consequently, the present invention should not be regarded as limited to any particular type of data logger system. However, by way of example, in one preferred embodiment, the data logger system may comprise a data logger system available from Campbell Scientific, Inc., of Logan, Utah, as model no. CR23X.

The exfiltrometer apparatus 10 may be operated as follows to estimate at least one unsaturated hydrologic property of the sample soil 22. First, an amount of soil 14 is provided to act as a sink for water contained in the soil sample 22. The soil 14 may comprise any of a wide range of soils, as would be obvious to persons having ordinary skill in the art after having become familiar with the teachings provided herein. Generally speaking, it is desirable to provide soil 14 having a tension of about 300 cm, although this is not required. The soil 14 may be provided in container 12, as best seen in FIG. 1. Then, the sample container 16 is positioned on the soil 14 in the container 12 so that the open end 18 of sample container 16 is resting on the soil 14. The sample container 16 is then filled with the sample soil 22 so that the sample soil 22 communicates with the soil 14 provided in the container 12. Water 36 from water supply 34 is then added to the sample soil 22 until the sample soil 22 is substantially saturated. As mentioned, the sample soil 22 is substantially saturated when the tensiometers 28 and 30 indicate saturated readings. Sample soil 22 is then allowed to dry. During the drying process, water 36 from the sample soil 22 is drawn into (i.e., absorbed by) the soil 14 provided in container 12. As the sample soil 22 dries, at least a surface water potential, a subsurface water potential, and a water content of the sample soil is sensed by the various sensors (e.g., 24, 28, 30, and 32). The sensed data are then collected by the data logger system 44 which estimates at least one unsaturated hydrologic property of the sample soil 22.

By way of example, multiple hydraulic gradients may be calculated between any two of the tensiometers e.g., 24, 28, and 30. Generally, the hydraulic gradients are calculated between the tensiometers (e.g., tensiometers 28 and 30) positioned below the surface tensiometer 24. However, any combination may be used depending on the characteristics of the soil being measured. For example, a hydraulic gradient may be computed from the difference in water potential between the second tensiometer 28 and the third tensiometer 30 and the difference in elevation between the second tensiometer 28 and the third tensiometer 30. When the numeric value of the flux is divided by the numeric value of the hydraulic gradient, the result is the unsaturated hydraulic conductivity. Hydraulic conductivity may be represented graphically versus water content and/or water potential.

Figure 5:
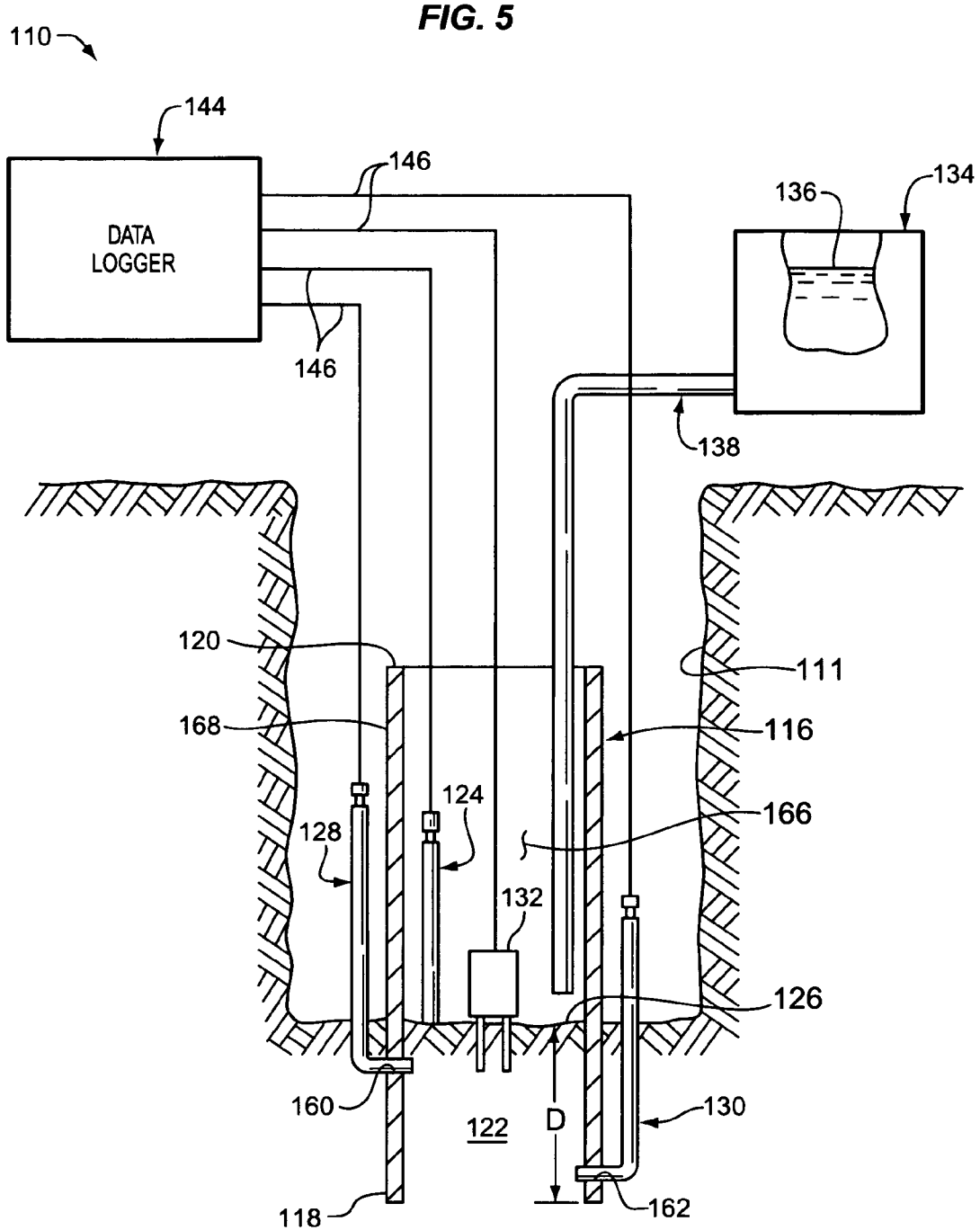
FIG. 5 is a side view schematic representation of another embodiment of exfiltrometer apparatus for determining unsaturated hydrologic properties of soil contained in a borehole.

A second embodiment 110 of an exfiltrometer suitable for estimating at least one hydrologic property of in-situ soil in a soil environment, such as in-situ soil in the bottom of a borehole 111, is illustrated in FIG. 5. The exfiltrometer 110 may comprise a sample container 116 defining a proximal end 120, a substantially open distal end 118, and an interior region 166 substantially between the proximal end 120 and distal end 118. The sample container 116 is positionable within the soil environment (e.g., the borehole 111) so that the distal end 118 of the sample container 116 penetrates to a depth D in-situ soil in the soil environment (e.g., a bottom surface 126 of the borehole 111). Accordingly, the sample container 116 isolates an in-situ soil sample 122.

The sample container 116 may comprise any of a wide range of configurations and may be fabricated from any of a wide range of materials that would be suitable for use in the borehole 111. Consequently, the sample container 116 should not be regarded as limited to any particular configuration or material. However, by way of example, in one preferred embodiment, the sample container 116 comprises a generally cylindrically shaped tube or pipe-like member having an internal diameter of about 15 cm and a length (i.e., height) of about 30 cm. The sample container 116 may be fabricated from any of a wide range of materials, such as steel or plastic, that would be suitable for use in the expected (e.g., borehole) environment. Consequently, the present invention should not be regarded as limited to any particular material. However, by way of example, in one embodiment, the sample container 116 is fabricated from metal.

The exfiltrometer apparatus 110 also includes a first tensiometer 124 that is operatively associated with the sample container 116 so that the first tensiometer 124 senses a surface water potential at about the surface 126 of the in-situ soil sample 122 isolated by the sample container 116. The first tensiometer 124 may be identical to the first tensiometer 24 described above for the first embodiment 10 of the exfiltrometer apparatus. Similarly, the first tensiometer 124 may be mounted within the sample container 116 in any of the manners described above for mounting the first tensiometer 24 within sample container 16. It should be noted that, if the first tensiometer 124 is mounted so that it extends through the side wall 168 of sample container 116, the first tensiometer 124 should be mounted so that the porous membrane (e.g., porous membrane 56' (FIG. 2) is flush with the interior surface of side wall 168. Alternatively, the tensiometer 124 should be mounted so that the porous membrane (e.g. 56') extends only a very slight distance (e.g., a few millimeters or so) past the side wall 168. This type of mounting arrangement will avoid creating a conduit for water adjacent the side wall 168 of sample container 116.

A second tensiometer 128 is operatively associated with the sample container 116 so that the second tensiometer 128 senses a first subsurface water potential below the surface 126 of the in-situ soil sample 122 isolated by the sample container 116. The sample container 116 may be provided with an opening 160 therein to allow the second tensiometer 128 to measure the first subsurface water potential. In the embodiment shown and described herein, the opening 160 provided in the sample container 116 is positioned so that the second tensiometer 128 will be located about 5 cm below the surface 126 of the in-situ soil sample 122 isolated by the sample container 116 when the sample container 116 has been made to penetrate the in-situ soil at the bottom 126 of the borehole 111. Alternatively, other distances may be used. It is generally preferred, but not required, that the second tensiometer 128 comprise a generally L-shaped tensiometer of the type described above and illustrated in FIG. 2. Such an L-shaped tensiometer configuration allows the exfiltrometer apparatus 110 to be more readily accommodated within the limited confines of the borehole 111. The second tensiometer 128 should also be mounted so that the porous membrane is either flush with the inside of side wall 168 or extends only slightly past (e.g., by a distance of a few millimeters or so) the side wall 168. This type of mounting arrangement will avoid creating a conduit for water adjace the side wall 168 of sample container 116.

As was the case for the exfiltrometer 10 of the first embodiment, the exfiltrometer 110 of the second embodiment may be provided with additional tensiometers, such as optional third tensiometer 130. The third tensiometer 130 is operatively associated with the sample container 116 so that the third tensiometer 130 senses a second subsurface water potential below the surface 126 of the in-situ soil sample 122 isolated by the sample container 116. The sample container 116 may be provided with an opening 162 therein to allow the third tensiometer 130 to measure the second subsurface water potential. In the embodiment shown and described herein, the opening 162 provided in the sample container 116 is positioned so that the third tensiometer 130 will be located about 10 cm below the surface 126 of the in-situ soil sample 122 isolated by the sample container 116 when the sample container 116 has been made to penetrate the in-situ soil (e.g., the bottom 126 of the borehole 111). Alternatively, other distances may be used. The third tensiometer 130 should also be mounted so that the porous membrane thereof is either flush with the inside of sidewall 168 or extends only slightly beyond the side wall 168.

The third tensiometer 130 may be substantially identical to the second tensiometer 128. It is also generally preferred, but not required, that the third tensiometer 130 comprise a generally L-shaped tensiometer of the type already described and illustrated in FIG. 2.

A water content sensor 132 may also be provided to sense a water content in the in-situ soil sample 122 isolated by the sample container 116. The water content sensor 132 may comprise any of the water content sensor embodiments and mounting configurations already described for the water content sensor 32 utilized in the first embodiment 10 of the exfiltrometer apparatus. The exfiltrometer apparatus 110 may also be provided with a water supply system 134 to supply water 136 to the in-situ soil sample 122 isolated by the sample container 116. The water 136 from the water supply system 134 may be delivered to the in-situ soil sample 122 via a suitable water conduit system 138 in the manner already described for the water supply system 34 of the first embodiment 10.

The various tensiometers 124, and 128 (and, optionally, tensiometer 130), as well as the water content sensor 132 are operatively connected to a data logger system 144 by any convenient means, such as, for example, via wire leads 146. The data logger system 144 may be identical to the data logger system 44, thus will not be described in further detail herein.

The exfiltrometer apparatus 110 may be operated as follows to determine at least one unsaturated hydrologic property of in-situ soil contained in a soil environment, such as in-situ soil contained within borehole 111. The sample container 116 is first positioned within the soil environment (e.g., the borehole 111) so that the distal end 118 of the sample container 116 penetrates to a depth D in-situ soil in the soil environment (e.g., the bottom surface 126 of the borehole 111). In the embodiment shown and described herein, the depth D may be selected to be in a range of about 15 cm to about 30 cm, although other depths may be used. At this position, the sample container 116 isolates an in-situ soil sample 122 within the interior region 166 defined by the sample container 116. Next, water 136 from the water supply 134 is introduced to the in-situ soil sample 122 until the in-situ soil sample 122 is substantially saturated. The in-situ soil sample 122 is then allowed to dry using the in-situ soil within the soil environment (e.g., the borehole 111) not isolated by the sample container 116 to pull water 136 from the in-situ soil sample 122 isolated by the sample container 116. Thereafter, the water potential and water content data values are sent to the data logger system 144 which determines at least one unsaturated hydrologic property of the in-situ soil sample 122.

EXAMPLE

Figure 6:
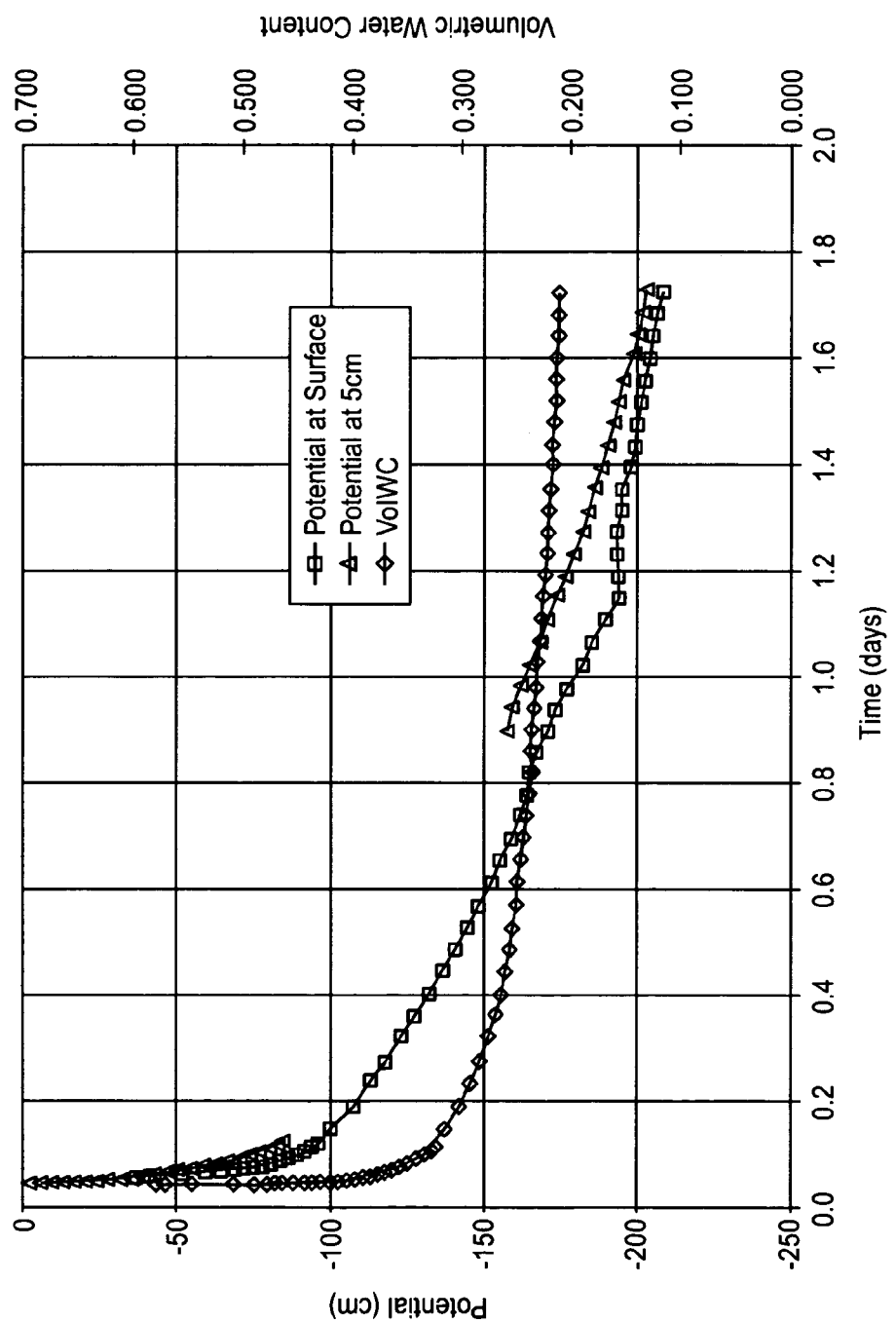
FIG. 6 is a graphical representation of unsaturated hydrologic data (i.e., water potential and water content as a function of time) obtained during a field test run.

FIGS. 6–9 present data from one of the first field exfiltrometer tests conducted on a silty loam soil. The surface exfiltrometer was set up substantially as shown in FIG. 1 with tensiometers (e.g., 24 and 28) located at the surface 26 of the sample soil 22 and at a depth of about 5 cm below the surface 26. Water was introduced at the surface 26 until the sample soil 22 was saturated. Excess water was removed and data collection commenced. FIG. 6 graphically represents the surface water potential sensed by the first (i.e., surface) tensiometer 24 and the subsurface water potential sensed by the second (i.e., subsurface) tensiometer 28 located about 5 cm below the surface 26 of the sample soil 22. Water content data sensed by the water content sensor 32 was also collected. All data were plotted as a function of time. While it is noted that data from the second or subsurface tensiometer 28 at 5 cm depth is not represented in the interval from 0.1 to about 0.9 day due to equipment failure, it is the inventors belief that extrapolation of the curve over this interval would be an accurate representation of the data that would have been obtained.

Figure 7:
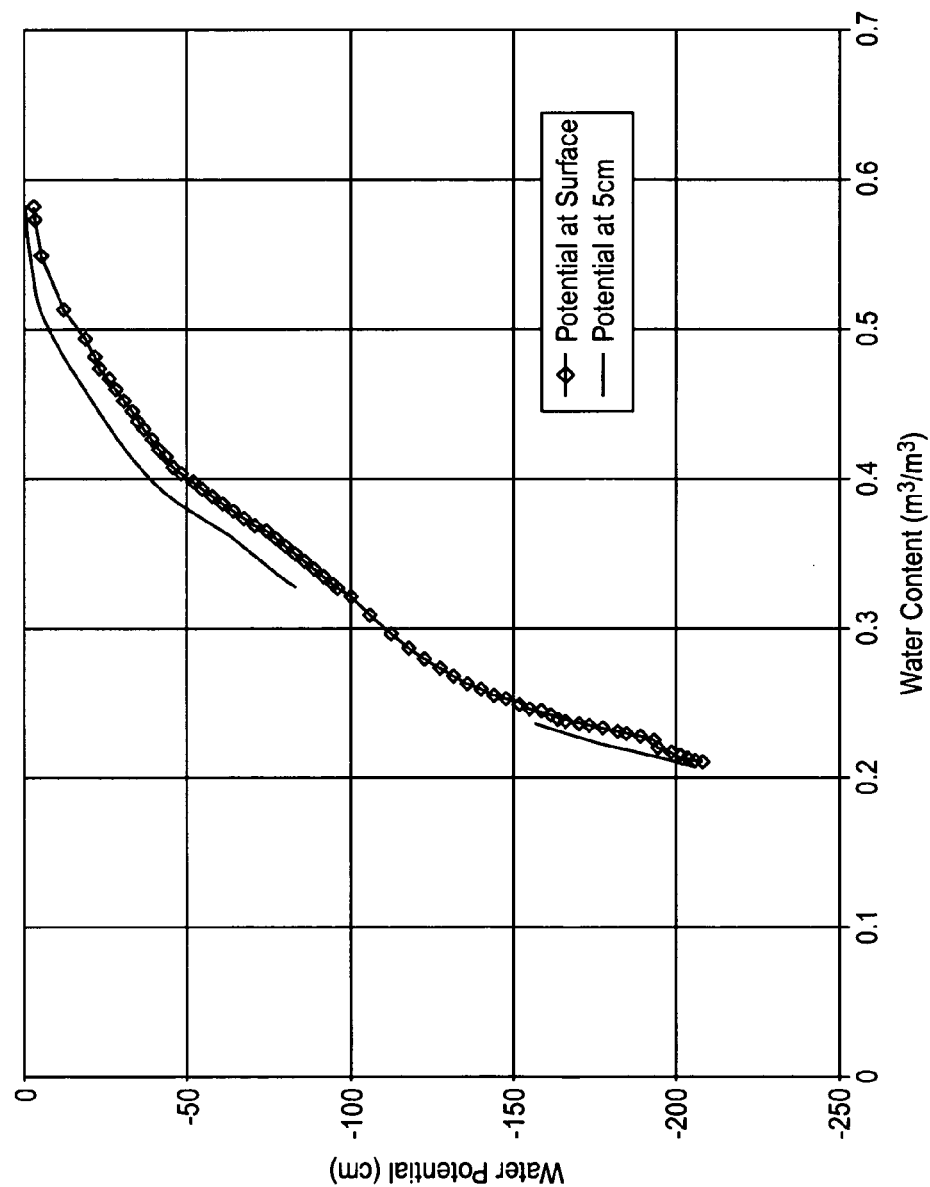
FIG. 7 is a graphical representation of unsaturated hydrologic data (i.e., water potential as a function of water content) obtained during a field test run.

The soil water retention curve (water potential versus water content) shown in FIG. 7 was obtained by plotting the water potentials against the water contents shown in FIG. 6 following the onset of drainage. FIG. 7 shows rapid changes in water potential near saturation followed by a slower change from about 150 cm of tension. The rapid change seen in the soil water potentials also indicated that the tensiometers were responding at a rate suitable to this type of experiment.

Figure 8:
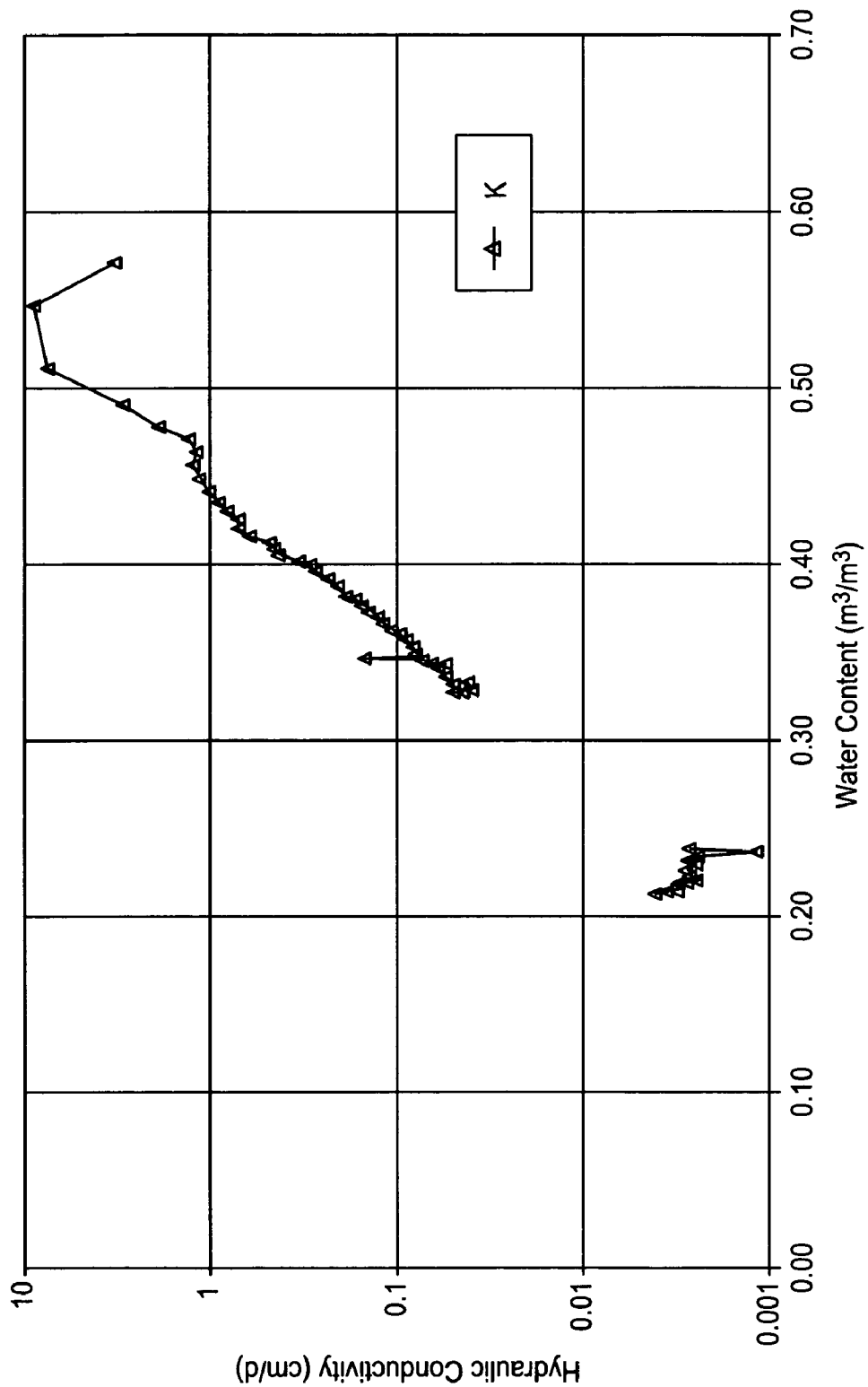
FIG. 8 is a graphical representation of unsaturated hydrologic data (i.e., hydraulic conductivity as a function of water content) obtained during a field test run.
Figure 9:
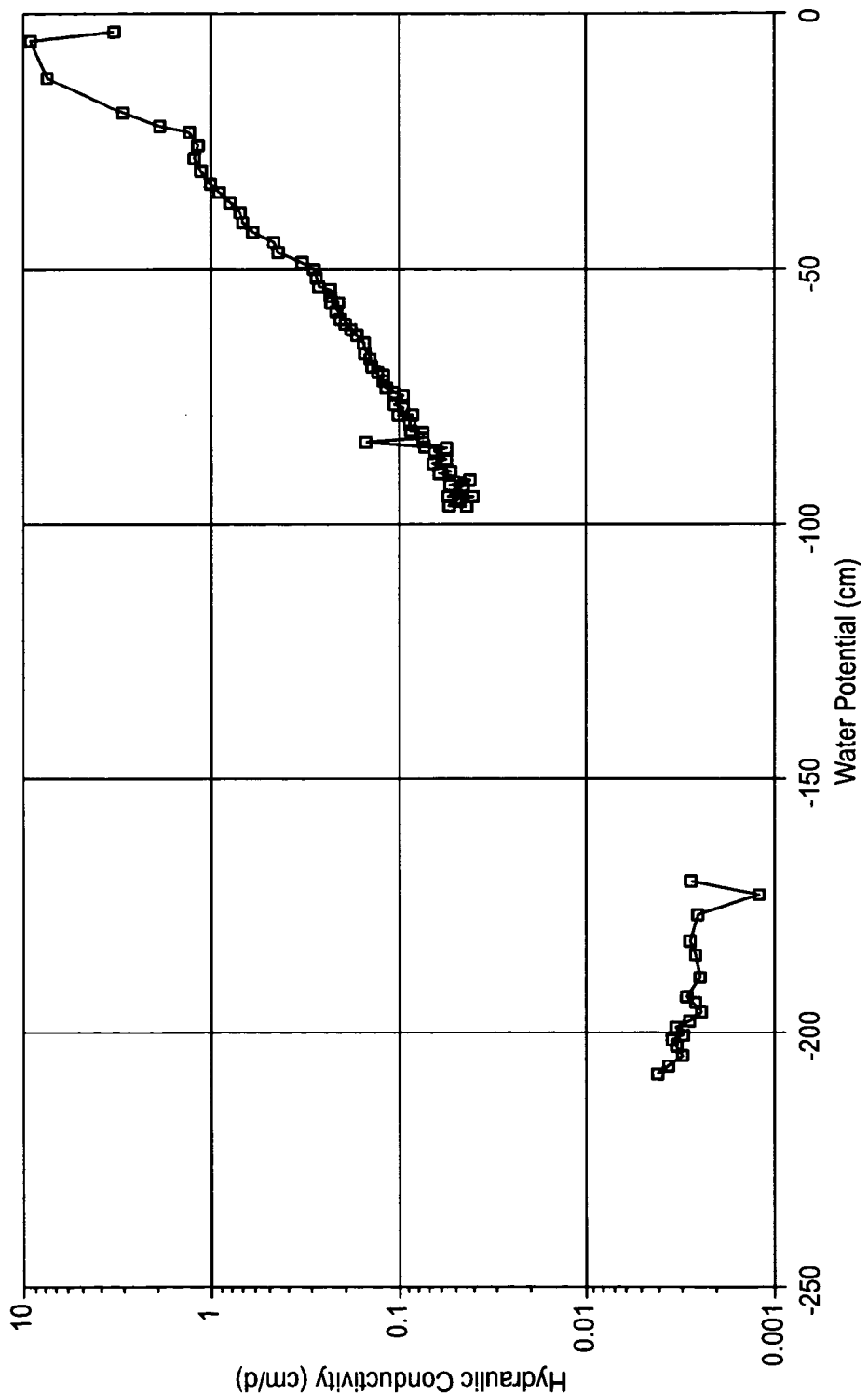
FIG. 9 is a graphical representation of unsaturated hydrologic data (i.e., hydraulic conductivity as a function of water potential) obtained during a field test run.

FIG. 8 shows the hydraulic conductivity to water content relationship where the hydraulic conductivity, as estimated by the Instantaneous Profile Method (IPM), was found to decrease following the onset of drainage. The hydraulic conductivity values from FIG. 8 were plotted against the soil water potentials and shown on FIG. 9.

It is contemplated that the inventive concepts herein described may be variously otherwise embodied and it is intended that the appended claims be construed to include alternative embodiments of the invention except insofar as limited by the prior art.

What is claimed is:

1. Exfiltrometer apparatus for estimating at least one unsaturated hydrologic property of sample soil, comprising:
 a container for holding soil;
 a sample container for holding the sample soil, said sample container being positionable with respect to said container when said container contains the soil so that the sample soil contained in said sample container is in communication with the soil contained in said container;

a first tensiometer operatively associated with said sample container so that said first tensiometer senses a surface water potential at about a surface of the sample soil contained in said sample container;

a second tensiometer operatively associated with said sample container so that said second tensiometer senses a first subsurface water potential below the surface of the sample soil contained in said sample container;

a water content sensor operatively associated with said sample container so that said water content sensor senses a water content in the sample soil contained in said sample container;

a water reservoir operatively associated with said sample container so that water from said water reservoir may be introduced to the sample soil contained in the sample container; and a data logger operatively connected to said first and second tensiometers, and to said water content sensor, said data logger receiving and processing data provided by said first and second tensiometers and by said water content sensor.

2. The apparatus of claim 1, wherein said sample container defines a first subsurface opening therein, said first subsurface opening being located at a first position below the surface of the sample soil contained within said sample container, said second tensiometer being operatively associated with said first subsurface opening so that said second tensiometer senses the first subsurface water potential.

3. The apparatus of claim 1, wherein said sample container defines a surface opening therein, said surface opening being located at about the surface of sample soil contained within said sample container, said first tensiometer being operatively associated with said surface opening so that said first tensiometer senses the surface water potential.

4. The apparatus of claim 1, further comprising a third tensiometer operatively associated with said sample container so that said third tensiometer senses a second subsurface water potential below the surface of the sample soil contained in said sample container, said third tensiometer being connected to said data logger.

5. The apparatus of claim 4, wherein said sample container defines a second subsurface opening therein, said second subsurface opening being located at a second position below the surface of the sample soil contained within said sample container, said second position being below said first position, said third tensiometer being operatively associated with said second subsurface opening so that said third tensiometer senses the second subsurface water potential.

6. The apparatus of claim 1, wherein said water content sensor comprises at least one probe, said water content sensor being positioned with respect to said second tensiometer so that said at least one probe is located at about same subsurface depth as a subsurface depth of the first subsurface water potential sensed by said second tensiometer.

7. The apparatus of claim 6, wherein said at least one probe of said water content sensor is mounted to an inner wall of said sample container.

8. The apparatus of claim 6, wherein said sample container defines at least one water content probe opening therein sized to receive said at least one probe of said water content sensor, so that said at least one probe of said water content sensor extends through said sample container into the sample soil contained within said sample container.

9. A method of estimating at least one unsaturated hydrologic property of sample soil, comprising:
  providing an amount of soil;
  positioning a sample container on the soil;
  filling the sample container with the sample soil so that the sample soil within the sample container communicates with the soil;
  adding water to the sample soil until the sample soil is substantially saturated;
  allowing the sample soil to dry by allowing the soil to absorb water from the sample soil contained in the sample container; and
  sensing at least a surface water potential, a subsurface water potential, and a water content of the sample soil as the sample soil dries.

10. The method of claim 9, wherein providing an amount of soil comprises providing an amount of soil having a tension of at least about 300 cm.

11. The method of claim 9, further comprising sensing a second subsurface water potential at a level below a level at which is sensed said subsurface water potential.

12. Exfiltrometer apparatus for estimating at least one unsaturated hydrologic property of in-situ soil contained in a soil environment, comprising:
  a sample container defining a proximal end, a substantially open distal end, and an interior region substantially between said proximal and distal ends, said sample container being positionable within the soil environment so that the distal end of said sample container penetrates to a depth in-situ soil in the soil environment, said sample container isolating an in-situ soil sample within the interior region defined by said sample container;
  a water supply operatively associated with said sample container so that water from said water supply may be introduced into the in-situ soil sample isolated by said sample container;
  a first tensiometer operatively associated with said sample container so that said first tensiometer senses a surface water potential at about a surface of the in-situ soil sample isolated by said sample container;
  a second tensiometer operatively associated with said sample container so that said second tensiometer senses a first subsurface water potential below the surface of the in-situ soil sample isolated by said sample container;
  a water content sensor operatively associated with said sample container so that said water content sensor senses a water content in the in-situ soil sample isolated by said sample container; and
  a data logger operatively connected to said first and second tensiometers and to said water content sensor, said data logger receiving and processing data provided by said first and second tensiometers and by said water content sensor.

13. The apparatus of claim 12, wherein said sample container defines a first subsurface opening therein, said first subsurface opening being located at a first position below the surface of the in-situ soil sample isolated by said sample container, said second tensiometer being operatively associated with said first subsurface opening so that said second tensiometer senses the first subsurface water potential.

14. The apparatus of claim 12, wherein said sample container defines a surface opening therein, said surface opening being located at about the surface of the in-situ soil sample isolated by said sample container, said first tensiometer being operatively associated with said surface opening so that said first tensiometer senses the surface water potential.

15. The apparatus of claim 12, further comprising a third tensiometer operatively associated with said sample container so that said third tensiometer senses a second subsurface water potential below the surface of the in-situ soil sample isolated by said sample container, said third tensiometer being connected to said data logger.

16. The apparatus of claim 12, wherein said sample container defines a second subsurface opening therein, said second subsurface opening being located at a second position below the surface of the in-situ soil sample isolated by said sample container, said second position being below said first position, said third tensiometer being operatively associated with said second subsurface opening so that said third tensiometer senses the second subsurface water potential.

17. The apparatus of claim 12, wherein said water content sensor comprises at least one probe, said water content sensor being positioned with respect to said second tensiometer so that said at least one probe is located at about same subsurface depth in the in-situ soil sample isolated by said sample container as a subsurface depth of the first subsurface water potential sensed by said second tensiometer.

18. The apparatus of claim 17, wherein said at least one probe of said water content sensor is mounted to an inner wall of said sample container.

19. The apparatus of claim 17, wherein said sample container defines at least one water content probe opening therein sized to receive said at least one probe of said water content sensor, so that said at least one probe of said water content sensor extends through said sample container into the in-situ soil sample isolated by said sample container.

20. A method of estimating at least one unsaturated hydrologic property of in-situ soil in a soil environment, comprising:

positioning a sample container defining a proximal end, a substantially open distal end, and an interior region substantially between the proximal and distal ends within the soil environment so that the distal end of said sample container penetrates to a depth in-situ soil in the soil environment, said sample container isolating an in-situ soil sample within the interior region defined by the sample container;

adding water to the sample container until the in-situ soil sample isolated by the sample container is substantially saturated;

allowing the in-situ soil sample to dry using soil within the soil environment and not isolated by said sample container to pull water from the in-situ soil sample isolated by the sample container; and sensing at least a surface water potential, a subsurface water potential, and a water content of the soil sample isolated by the sample container as the soil dries.

21. The method of claim 20, further comprising sensing a second subsurface water potential at a level below a level at which is sensed said subsurface water potential.

* * * * *